United States Patent [19]

Strunk et al.

[11] 4,209,452

[45] Jun. 24, 1980

[54] ORGANOTIN SULFINATES AS INSECTICIDES AND ACARICIDES

[75] Inventors: Richard J. Strunk, Cheshire; Winchester L. Hubbard, Woodbridge; Shih-Yu Ma, Cheshire, all of Conn.

[73] Assignee: Uniroyal, Inc., New York, N.Y.

[21] Appl. No.: 878,203

[22] Filed: Feb. 16, 1978

Related U.S. Application Data

[62] Division of Ser. No. 691,186, May 28, 1976, Pat. No. 4,089,972.

[51] Int. Cl.$^2$ .............................................. C01F 7/22
[52] U.S. Cl. ................................. 260/429.7; 424/288
[58] Field of Search ...................................... 260/429.7

[56] References Cited

U.S. PATENT DOCUMENTS

| | | | |
|---|---|---|---|
| 3,031,483 | 4/1962 | Koopmans | 260/429.7 |
| 3,703,588 | 11/1972 | Idito et al. | 260/429.7 X |
| 3,794,670 | 2/1974 | Peterson | 260/429.7 |
| 3,850,970 | 11/1974 | Peterson et al. | 260/429.7 |

OTHER PUBLICATIONS

Kong et al., J.A.C.S. 93 3791, 3792 (1971).
Fong et al., J. Organometallic Chem. 22, pp. 95–106 (1970).

*Primary Examiner*—Helen M. S. Sneed
*Attorney, Agent, or Firm*—Anthony Lagani, Jr.

[57] ABSTRACT

Organotin sulfinates are useful for controlling insects and acarids. Certain of these organotin sulfinates are novel compounds.

8 Claims, No Drawings

ORGANOTIN SULFINATES AS INSECTICIDES AND ACARICIDES

This is a division of application Ser. No. 691,186 filed May 28, 1976, now U.S. Pat. No. 4,089,972.

BACKGROUND OF THE INVENTION

This invention relates to compounds of the generic formula:

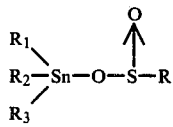

which have been found useful as insecticides and acaricides. Moreover, the level of application of the compounds of the invention required to control the insect and acarid pests is such as to minimize injury (phytotoxicity) to the crop plants.

Koopmans in U.S. Pat. No. 3,097,999 and U.S. Pat. No. 3,031,483 discloses, as prior art, compounds of the structure

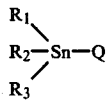

wherein $R_1$, $R_2$ and $R_3$ can be the same or different and represent alkyl groups with 1–12 carbon atoms, phenyl groups or phenyl groups substituted by a chlorine or bromine atom. Among the stated definitions for Q was —$SO_2C_6H_4.CH_3$ (p). These compounds disclosed by Koopmans were stated as having biocide and, in particular, fungicide and bactericide properties.

THE INVENTION

The compounds utilized in this invention are organotin sulfinates having the general formula

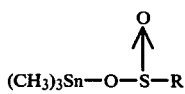

wherein R is selected from the group consisting of aryl; aryl substituted by phenyl, one or more halogens, one to three straight chain or branched alkyls having from 1 to 18 carbon atoms and cycloalkyl having 4 to 8 carbon atoms; and

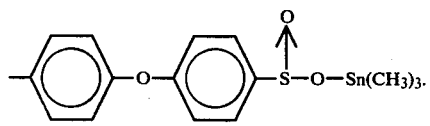

The trimethyltin sulfinate compounds are preferred as insecticides over related sulfinates in which other organic substituents are attached to the Sn because the effective rates of application are lower for the trimethyltin sulfinates and thereby less injury is caused to the crops on which they are applied.

The novel compounds of this invention are those corresponding to the above general formula wherein R is selected from the group consisting of alkylphenyl in which the alkyl substituent has 4 to 10 carbon atoms, cycloalkylphenyl, halophenyl and

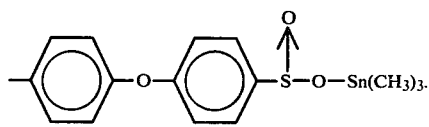

The following equations illustrate various methods available for the preparation of the compounds utilized in this invention:

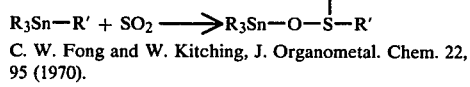

C. W. Fong and W. Kitching, J. Organometal. Chem. 22, 95 (1970).

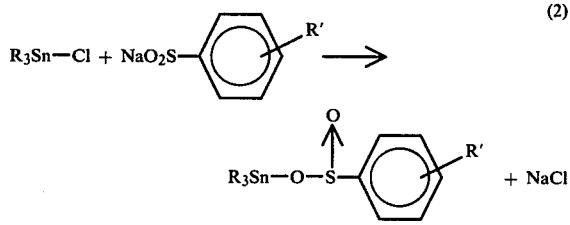

(a) G. A. Razuvaev, Y. I. Dergunov and N. S. Vyazankin, Zh. Obshch. Khim 32, 2515 (1962), C.A. 58, 9111g.
(b) P. M. Slagan, Ph.D. Thesis, University of North Carolina, 1967.

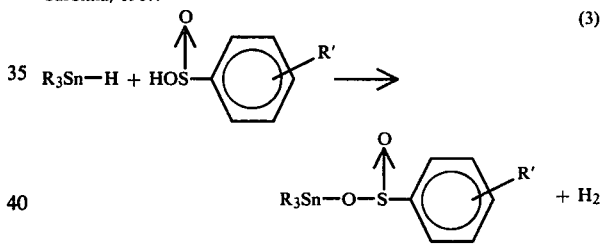

E. I. Becker and M. Pang, J. Org. Chem. 29, 1948 (1964).

Trimethyltin chloride was employed in the procedure illustrated by equation 2. The following sodium arenesulfinates were also employed as starting materials in the procedure of equation 2:
sodium benzenesulfinate;
sodium p-toluenesulfinate;
sodium p-t-butylbenzenesulfinate;
sodium p-t-pentylbenzenesulfinate;
sodium p-bromobenzenesulfinate;
sodium p-chlorobenzenesulfinate;
sodium p-cyclopentylbenzenesulfinate;
sodium p-cyclohexylbenzenesulfinate;
sodium p-cyclooctylbenzenesulfinate;
disodium 4,4′-oxybisbenzenesulfinate;
sodium 2-tetralinsulfinate;
sodium 5-phenyl-1-naphthalenesulfinate;
sodium 8-phenyl-2-naphthalenesulfinate;
sodium 5-fluoro-1-naphthalenesulfinate;
sodium 8-chloro-2-naphthalenesulfinate;
sodium 5-bromo-1-naphthalenesulfinate;
sodium 8-iodo-2-naphthalenesulfinate;
sodium 5-methyl-1-naphthalenesulfinate;
sodium 8-ethyl-2-naphthalenesulfinate;
sodium 5-butyl-1-naphthalenesulfinate;

sodium 8-t-butyl-2-naphthalenesulfinate;
sodium 5-octyl-1-naphthalenesulfinate;
sodium 8-t-octyl-2-naphthalenesulfinate;
sodium 5-decyl-1-naphthalenesulfinate;
sodium 8-dodecyl-2-naphthalenesulfinate;
sodium 5-pentadecyl-1-naphthalenesulfinate;
sodium 8-octadecyl-2-naphthalenesulfinate;
sodium 5-cyclobutyl-1-naphthalenesulfinate;
sodium 5-cyclopentyl-1-naphthalenesulfinate;
sodium 8-cyclohexyl-2-naphthalenesulfinate;
sodium 5-cyclooctyl-1-naphthalenesulfinate; and
sodium 8-cyclooctyl-2-naphthalenesulfinate.

These compounds can be prepared by the method of Kulka, J.A.C.S. 72, 1215 (1950) from the corresponding sulfonyl chlorides.

The following example illustrates the method of equation 2:

EXAMPLE 1

To a solution of 8.0 g (40 mmoles) of trimethyltin chloride in 50 ml of acetone in a 250 ml Erlenmeyer flask was added dropwise at room temperature a solution of 9.75 g (40 mmoles) of sodium p-bromobenzenesulfinate in 100 ml of water. The reaction mixture was stirred overnight at room temperature. The reaction mixture was filtered and 5.0 g of a solid were obtained. The solid, m.p. 254°–257° C. with decomposition, was characterized as a mixture of dimethyltin bis(p-bromobenzenesulfinate) and the desired product. Acetone was evaporated from the aqueous filtrate affording 4.3 g of a solid trimethyltin p-bromobenzenesulfinate, m.p. 146° C. with decomposition. The NMR spectrum showed the following: The aromatic protons appeared as two multiplets each centered at 754 and 734 Hz (each having 2 protons); the trimethyltin protons appeared as a singlet at 56 Hz flanked on either side by satellite bands (9 protons). Analysis: Calc'd for $C_9H_{13}BrO_2SSn$ (percent): C, 28.16; H, 3.41; S, 8.35; Sn, 30.92. Found: C, 28.10; H, 3.56; S, 8.55; Sn, 30.19.

EXAMPLE 2

Using the procedure described in Example 1, additional organotin compounds were prepared and, along with the product of Example 1, are identified in Table I below. In many cases, the compounds needed no further purification whereas, in others, they were recrystallized from an appropriate solvent.

Table I

| No. | Substituents Attached to Sn of Sn—O—S—R | | | R | Reaction Solvent | Purification Method | M.P. °C. |
|---|---|---|---|---|---|---|---|
| 1 | $CH_3$ | $CH_3$ | $CH_3$ | —C₆H₄—Br | Acetone/water | None | 146 with decompn. |
| 2 | " | " | " | —C₆H₄—Cl | Acetone/water | Recrystallization | 119–121.6 |
| 3 | " | " | " | —C₆H₃Cl₂ (2,-Cl; -Cl) | Diethyl ether | Recrystallization | 126.3–128.8 |
| 4 | " | " | " | —C₆H₅ | H₂O/acetone | Washing with acetone & H₂O | 78–80 |
| 5 | " | " | " | —C₆H₄—$CH_3$ | H₂O/acetone | None | 98–102 |
| 6 | " | " | " | —C₆H₄—$C(CH_3)_3$ | Ethanol/water | None | 173–175 with decompn. |
| 7 | " | " | " | —C₆H₄—$C(CH_3)_2CH_2CH_3$ | H₂O/acetone | Recryst. from $CH_3OH$—$H_2O$ | 161–3 |
| 8 | " | " | " | —C₆H₄—(2-thienyl) | H₂O/acetone/ EtOH | Recryst. from MeOH | 169–73 |
| 9 | " | " | " | —C₆H₄—(benzothienyl) | H₂O/MeOH/ acetone | Recryst. from $CH_3OH$ | 270 (dec.) |

Table I-continued

| No. | Substituents Attached to Sn of Sn—O—S—R ↑ | R | Reaction Solvent | Purification Method | M.P. °C. |
|---|---|---|---|---|---|
| 10 | " " " | [cycloheptyl-phenyl structure with S] | H₂O/acetone | Recryst. from ethyl acetate | 148–50 |
| 11 | " " " | [phenyl-O-phenyl-S(=O)—O—Sn(CH₃)₃ structure] | Dioxane/H₂O/ acetone | Recryst. from DMSO-H₂O | >335 |

Compound #3 (Table I) was prepared by the method illustrated in equation 3.

EXAMPLE 3 (Compound #3)

A 100 ml three-necked flask, fitted with a reflux condenser and addition funnel, was flushed thoroughly with nitrogen and charged with 4.5 ml (29.4 mmoles) of a solution of trimethyltin hydride in xylene (78 volume/volume %). To this solution was added dropwise with stirring at room temperature 70 ml of a solution of 6.0 g (28.5 mmoles) of 2,5-dichlorobenzenesulfinic acid in diethyl ether. Evolution of hydrogen occurred immediately and throughout the addition which lasted one hour. The flask was cooled in ice-water, and 9.38 g of solid was collected on a filter. The solid was recrystalized from cyclohexaneligroin giving 9.28 g of trimethyltin 2,5-dichlorobenzenesulfinate, m.p. 126.3°–128.8° C. The presence of strong absorption bands at 950 and 980 cm⁻¹, characteristic of the

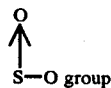
S—O group in organotin sulfinates, was observed in the infrared spectrum (KBr). The NMR spectrum showed the following characteristics: The aromatic proton ortho to the sulfinato group appeared as a multiplet centered at 765 Hz (1 proton); the remaining aromatic protons appeared as a multiplet centered at 727 Hz (2 protons); the protons of the trimethyltin group appeared as a singlet at 62 Hz flanked on either side by two satellite bands (9 protons).

Analysis: Calc'd for C₉H₁₂Cl₂O₂SSn (percent): C, 28.91; H, 3.23; Sn, 31.75. Found: C, 28.49; H, 3.04; Sn, 32.03.

The trimethyltin hydride is prepared by known procedures such as are described in the following references:

K. Hayashi, J. Iyoda and I. Shiihara, *J. Organometal. Chem.*, 10, 81 (1967).

H. G. Kuivila, *Advan. Organometal. Chem.*, 1, 47 (1964).

W. P. Neumann, *Angew. Chem., Internat. Edit.*, 2, 165 (1963).

Application of the compounds utilized in this invention as insecticides and acaricides can be carried out in a number of ways. For practical applications, the compounds can be used alone, or dissolved or suspended in suitable carriers such as water, alcohols, ketones, phenols, toluene or xylenes. Optionally, one or more surface active agents and/or inert diluents can be added to the formulation to facilitate handling. The formulations can take the form of dusts, granules, wettable powders, pastes, emulsifiable concentrates, or a water soluble solid.

For example, the compounds utilized in this invention can be applied as dusts when admixed with or absorbed on powdered solid carriers, such as the various mineral silicates, e.g., mica, talc, pyrophillite and clays, or as liquids or sprays when in a liquid carrier, as in solution in a suitable solvent such as acetone, benzene or kerosene, or dispersed in a suitable non-solvent medium, for example, water. In protecting plants (the term includes plant parts), the chemicals are preferably applied as aqueous emulsions containing a surface-active dispersing agent which may be an anionic, nonionic or cationic surface-active agent. Such surface-active agents are well known and reference is made to U.S. Pat. No. 2,547,724, columns 3 and 4, for detailed examples of the same. The chemicals may be mixed with such surface-active dispersing agents, with or without an organic solvent, as concentrates for subsequent addition of water to make aqueous suspensions of the chemicals of the desired concentration. The chemicals may be admixed with powdered solid carriers, such as mineral silicates together with a surface-active dispersing agent so that a wettable powder is obtained which may then be applied directly to loci to be protected, or may be shaken with water to form a suspension of the chemical (and powdered solid carrier) in water for application in that form. The chemicals may be applied to loci to be protected by the aerosol method. Solutions for aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in a less volatile solvent and then admixing such solution with the highly volatile liquid aerosol carrier. The chemicals may be used admixed with carriers that are active themselves, for example: insecticides, acaricides, fungicides or bactericides.

These formulations will contain amounts of the compounds effective for the particular method of control. These amounts can vary widely; typically, the range is from 0.1 to 95% active ingredient. Spray dilutions can contain from a few parts per million to full strength concentrates applied by ultra low volume techniques. Concentration per unit area, where plants are the area treated, can vary from 0.01 to 10 pounds per acre, and preferably from 0.1 to 0.5 pound per acre.

Commonly, the compounds are applied directly. To control aphids, for example, sprays of the compounds are applied to the aphids directly, to plants upon which they feed, or both. Sprays applied to the aphid infested plants kill effectively even if directly contact does not occur, as where the aphids cling to the inner surface of a curled up leaf or lie in a protected leaf sheath of, for example, a grain plant. Another effective method of attack involves application of the compounds to the soil or other medium in which insect-infested plants live. The compounds act systemically upon the insects after the compound is absorbed by the plants.

Compounds of the invention are particularly valuable for use on spray tolerant crops such as soybeans, corn, potatoes, cabbage, tobacco, alfalfa, peanuts and apples which are not adversely affected by the low concentration of these compounds needed to control insect pests. They also are valuable for post harvest applications, for example, fall applications to cotton to destroy cotton boll weevils before they attain overwinter diapause and applications on trap crops deliberately planted to attract insect pests so that they can be destroyed in a concentrated area and the planting then plowed under.

Harmful insects and arachnids, such as mites, attack a wide variety of plants, including both ornamental and agricultural plants such as chrysanthemum, azalea, cotton, corn, wheat, apple and tobacco, and inflict damage by withdrawing vital juices from the plants, by secreting toxins and often by transmitting diseases. The compounds utilized in this invention can prevent such damage. The methods of application, and the selection and concentration of these compounds will, of course, vary depending upon such circumstances as area, climate, prevalent diseases, plant tolerance, etc. One skilled in the art can select the proper approach by simple experiments.

The compounds of this invention are also useful as insecticides and acaricides against industrial, forest, household and farm insects and acarids.

EXAMPLE 4

The organotin compounds of this invention were tested as insecticides and acaricides according to the following procedures:

A. Mosquito Larvae Test

Formulations were prepared by dissolving 30 mg of organotin compound of the invention in 10 ml of acetone. This solution was then diluted to 10 ppm and to 1 ppm with water. Two 25-ml aliquots were placed in test tubes to which were added 10 to 25 fourth instar larvae of the yellow fever mosquito, *Aedes aegypti* (Linnaeus). The tubes were held in darkness for 72 hours. At the end of this period the percent control was determined.

B. Aphid Contact Test

Test formulations were prepared for spraying at 100 ppm (parts per million) concentration by dissolving them in a small amount of acetone and adding a suitable wetting agent. Typically, 0.6 gram of organotin compound was dissolved (or suspended) in 10 ml of acetone, 2 drops of Triton-X100 wetting agent (octylphenoxy polyethoxy ethanol with 9-10 mole percent of polyethylene oxide) were added and this was suspended in 300 ml of water to make a 6000 ppm suspension. An aliquot was then further diluted with distilled water to 100 ppm concentration of organotin compound.

Eight to ten day old barley seedlings, grown ten plants each in a 12 oz. cup, were infested with corn leaf aphids *Rhopalosiphum maidis* (Fitch), two days prior to treatment. Two pots were treated with each formulation by spraying with a spray atomizer while the plants were rotating on a turntable. Following treatment, the plants were held for 5 days in the greenhouse. At the end of this period, the percent control of the aphids was estimated based on the reduction of the population density as compared to untreated plants used as controls.

C. Tobacco Bud Worm Diet Test

Test formulations were prepared at 1000 ppm and 100 ppm as in B, the Aphid Contact Test, above. Two-tenth ml of the diluted formulations was pipetted onto the surface of 5 grams of a synthetic diet mixture held in partially filled cells of a plastic jelly tray. Five cells were treated with each chemical dilution. The diet mixture was a modified Vanderzant diet consisting of wheat germ, soy flour, agar, sugar, salts, vitamins, preservatives and water. The jelly trays had fifty cavities per sheet, each cavity being approximately $2.5 \times 4.0 \times 1.5$ cm.

Following treatment, a third or early fourth instar larva of the tobacco bud worm, *Heliothis virescens* (Fabricius), was placed in each cell. The trays were then covered with a plastic film plus a sheet of rigid plastic and were held in an incubator at 80° F.

At the end of one week, the trays were examined and the percent control was determined, adjusted for any natural mortality in the controls by Abbott's formula. The trays were held an additional week and any abnormalities in the development of the survivors was noted.

D. Tobacco Bud Worm Test on Cotton and Soybeans

Organotin sulfinates of this invention were sprayed on plants for the control of tobacco budworm larvae, a lepidopterous pest which feeds on a number of host plants such as tobacco, cotton, soybeans and also a number of solanaceous plants where it attacks the foliage and commonly destroys the new buds.

Spray suspensions of these sulfinates were prepared by dissolving 10 mg of chemical in 1 ml of acetone, adding 1 drop of a surfactant Emulfor EL 719 and diluting with water to a volume of 100 ml for a concentration of 100 ppm.

Cotton four weeks old and soybeans three weeks old, grown from seed under 75° F. greenhouse condition, were used in these tests. Cotton (two replicates) and soybeans (six replicates) were treated with the water suspension, which was applied with a spray atomizer evenly to the foliage. The following day one third instar tobacco budworm larva was placed on each replicate and confined by a netting of cheesecloth. Ten untreated soybeans and ten untreated cotton plants were used for controls.

One week following spray treatment the number of surviving larvae were determined, feeding damage was compared to that found on the untreated controls and phytotoxicity was recorded.

E. Cotton Boll Weevil Test

Formulations were prepared at 100 ppm as in B, the Aphid Contact Test, above. Cotton seedlings 12 to 14 days old grown in 12 oz cups were used. Two pots were treated with each formulation by spraying with a spray atomizer while rotating the pots on a turntable. Five adult cotton boll weevils, *Anthonomous grandis* Boheman, were placed in each pot following treatment and were caged by covering the pots with an inverted 16 oz styrofoam cup with small perforations punched in the bottom. The surviving weevils were counted after five days in the greenhouse to determine the percent control, corrected for any natural mortality in the control plants by Abbott's formula. The percent reduction in feeding was estimated by visual comparison of the feeding damage to the treated plants with the control (untreated) plants.

F. Mexican Bean Beetle Larvae Test on Pinto Beans

Pinto beans two weeks old were treated with spray suspension in the same manner as that used in D, the tobacco budworm test, above. Two replicates were treated with 100 ppm sprays and five larvae were placed on each replicate, when the spray deposit had dried. Observations of larvae, feeding damage and phytotoxicity were made after five days.

G. Mite One-Day Residual Test

Test compounds were prepared as in B, the Aphid Contact Test, above, but were further diluted to 100 ppm with water.

Cotton, in the second primary leaf stage grown in twelve ounce cups under greenhouse conditions at 70°–75° F., was used in the test.

One plant (two primary leaves) in one pot was used for each replicate; two replicates were used for each concentration of organotin compound tested.

The plants were sprayed with the dispersions using a small spray atomizer to thoroughly drench the foliage.

One day following treatment, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves. On an estimation basis in comparison with the number of living mites on the control plants, the percent control was determined.

H. Abbott's Formula $$\text{Adjusted \% Control} = \frac{\% \text{ alive in check} - \% \text{ alive in treated } (\times 100)}{\% \text{ alive in check}}$$

The above formula was used to correct for natural mortality when calculating % Control. Natural mortality was detectable and corrections made in calculating % Control of tobacco bud worms (with tests both on diet and on plants), cotton boll weevils, and Mexican bean beetle larvae where the numbers of the insects present at the start and the end of the test period were known.

Abbott's Formula was also adapted to calculate the % Reduction of Feeding by tobacco bud worms, cotton boll weevil and Mexican bean beetle larvae as follows:

$$\text{\% Reduction of Feeding} = \frac{\% \text{ feeding damage on check plants} - \% \text{ feeding damage on treated plants } (\times 100)}{\% \text{ feeding damage on check plants}}$$

The results of the above-described tests are set forth in Table II below, the compound numbers corresponding to those in Table I above.

Table II

| | Organotin Sulfinates as Insecticides and Acaricides | | | | | | | | | |
|---|---|---|---|---|---|---|---|---|---|---|
| | % Control Mosquito Larvae | | % Control Aphids | % Control* Tobacco Bud Worm-Diet Test | | | Tobacco Budworm-1 Day Residual Test | | | |
| | | | | | | | Cotton 100 ppm | | Soybeans 100 ppm | |
| Compound No. | 10 ppm | 1 ppm | 100 ppm | 1000 ppm | 100 ppm | 20 ppm | % Control | % Reduction Feeding* | % Control* | % Reduction Feeding* |
| 1 | 100 | 100 | 90 | 100 | 100 | - | 0 | 82 | 60 | 100 |
| | - | 92 | | | | | | | | |
| 2 | 100 | 8 | 90 | 100 | 100 | 80 | 100 | 91 | 100 | 98 |
| 3 | 100 | 0 | 90 | 100 | 100 | 80 | 100 | 41 | 100 | 98 |
| 4 | 82 | 0 | - | 100 | 100 | 42 | 50 | 95 | 100 | 95 |
| | | | | - | 100 | 6 | | | | |
| 5 | 100 | 0 | - | 100 | 100 | 53 | 100 | 91 | 100 | 91 |
| | 100 | 21 | | | | | | | | |
| 6 | 100 | 0 | 90 | 100 | 100 | 60 | 100 | 90 | 84 | 91 |
| 7 | 100 | 0 | 20 | 100 | 80 | 20 | 100 | 90 | 84 | 98 |
| 8 | 100 | 0 | 60 | 80 | - | - | 100 | 93 | 66 | 100 |
| 9 | 100 | 100 | 40 | 100 | 100 | - | 100 | 82 | 50 | 91 |
| 10 | 100 | 85 | 0 | 100 | 20 | - | 0 | 72 | 84 | 98 |
| 11 | 100 | 0 | 90 | 100 | 100 | 80 | 100 | 97 | 100 | 89 |

| Compound No. | % Control* Cotton Boll Weevil 100 ppm | Boll Weevil % Feeding Reduced* on Cotton 100 ppm | Mexican Bean Beetle | | Mite One-Day Residual 100 ppm |
|---|---|---|---|---|---|
| | | | % Control* 100 ppm | Larvae % Reduction of Feeding* 100 ppm | |
| 1 | 60 | 40 | 47 | 50 | 100 |
| | | | | | 64 |
| 2 | 87 | 90 | 79 | 66 | 80 |
| 3 | 11 | 70 | 58 | 50 | 75 |
| 4 | - | - | 95 | 66 | - |
| 5 | 63 | 70 | 95 | 66 | - |
| | 44 | 80 | | | |
| 6 | 44 | 80 | 58 | 50 | 25 |
| | | | | | 0 |
| 7 | 40 | 66 | 79 | 66 | 25 |
| | | 70 | | | |
| 8 | 53 | 0 | 58 | 66 | 96 |
| 9 | 90 | 80 | 79 | 50 | 25 |

Table II-continued
Organotin Sulfinates as Insecticides and Acaricides

| | | | | | |
|---|---|---|---|---|---|
| 10 | 33 | 10 | 47 | 50 | 25 |
| | 60 | 80 | | | |
| 11 | 44 | 66 | 58 | 66 | 90 |

Note: Presence of hyphen denotes that test was not run.
*Adjusted by use of Abbott's Formula.

As can be seen from the results set forth in Table II, the trimethyltin sulfinates utilized in this invention exhibit good to superior insecticidal and acaricidal activity for a wide variety of insects and acarids.

The phytotoxicity of the organotin sulfinates of this invention was observed in certain of the tests, and the results are reported in Table III. Phytotoxicity has reference to causing injury to or retardation of the growth of the host plants. A phytotoxicity rate of 20% or higher is considered unacceptable commercially.

Table III
Organotin Sulfinates - Phytotoxicity Observations

| | % Phytotoxicity (after one week) | | % Phytotoxicity (after 5 days) | |
|---|---|---|---|---|
| Compound No. | Cotton 100 ppm | Soybeans 100 ppm | Pinto Beans 100 ppm | Barley 100 ppm |
| 1 | 13* | .5* | 20 | 50 |
| 2 | 6* | 3.5* | 23 | 13* |
| 3 | 13* | 1.5* | 40 | 40 |
| 4 | 20 | 2.5* | 40 | 40 |
| 5 | 20 | 4.5* | 60 | 40 |
| 6 | 4.5* | 1.0* | 11* | 30 |
| 7 | 20 | 1.0* | 1.5* | 30 |
| 8 | 1.5* | 0.5* | 20 | 13* |
| 9 | 6* | 0* | 0* | 6* |
| 10 | 13* | 0* | 1.5* | 13* |
| 11 | 20 | 2.5* | 13* | 40 |

*Tolerant to phytotoxicity at 100 ppm.

The following conclusions can be drawn from the data presented in Tables II and III:

1. Satisfactory mosquito larvae control for all eleven exemplified compounds. Effective rates are 1 ppm for compounds #1 and #9, while 10 ppm is effective as a rate for the other nine compounds.

2. Tobacco bud worms were controlled at 100 ppm on both cotton and soybeans. Soybeans were tolerant at this rate to all eleven compounds. Cotton is tolerant at 100 ppm to compounds #1, 2, 3, 6, 8, 9 and 10.

3. Cotton boll weevil control has been demonstrated at 100 ppm with compounds #2 and 9 and cotton was tolerant of these compounds. Use of the other nine compounds for control of cotton boll weevils would be restricted by phytotoxicity to post harvest sprays or trap crop sprays where the plants are expendible and higher rates could be applied.

4. Compound #2 at 100 ppm was found to provide effective aphid control at an acceptable phytotoxicity level on barley.

5. Compounds #1 and #8 at 100 ppm provide effective mite control at an acceptable phytotoxicity level on cotton.

However, all of the compounds of this invention can be advantageously used at effective levels against insects and acarids on apples, corn, potatoes, tobacco, cabbage, soybeans, alfalfa, peanuts and other tolerant crops.

What is claimed is:

1. An organotin compound having the general formula

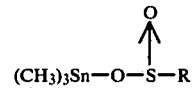

wherein R is selected from the group consisting of (1) alkylphenyl in which the alkyl substituent has 4 to 10 carbon atoms, (2) cycloalkylphenyl, (3) 2,5 dichlorophenyl, and

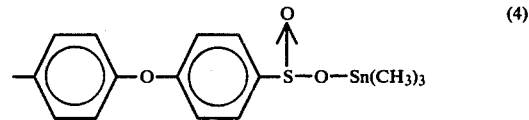
(4)

2. The compound of claim 1 wherein said compound is trimethyltin p-t-butylbenzenesulfinate.

3. The compound of claim 1 wherein said compound is trimethyltin p-t-pentylbenzenesulfinate.

4. The compound of claim 1 wherein said compound is trimethyltin p-cyclopentylbenzenesulfinate.

5. The compound of claim 1 wherein said compound is trimethyltin p-cyclohexylbenzenesulfinate.

6. The compound of claim 1 wherein said compound is trimethyltin p-cyclooctylbenzenesulfinate.

7. The compound of claim 1 wherein said compound is di(trimethyltin)p,p'-oxybisbenzenesulfinate.

8. The compound of claim 1 wherein said compound is trimethyltin 2,5-dichlorobenzenesulfinate.

* * * * *